United States Patent
Eubanks et al.

(10) Patent No.: US 9,649,437 B2
(45) Date of Patent: May 16, 2017

(54) INTERVENTIONAL CATHETER ASSEMBLIES AND CONTROL COMPONENTS FOR INTERVENTIONAL CATHETER ASSEMBLIES

(71) Applicant: Boston Scientific Limited

(72) Inventors: Shannon Eubanks, Woodinville, WA (US); Richard Van Bibber, Redmond, WA (US); Michael David Nelson, Seattle, WA (US); Nicolas Guillame Hostein, Seattle, WA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 400 days.

(21) Appl. No.: 13/830,718

(22) Filed: Mar. 14, 2013

(65) Prior Publication Data

US 2014/0276390 A1    Sep. 18, 2014

(51) Int. Cl.
*A61M 5/172* (2006.01)
*A61M 1/00* (2006.01)
(Continued)

(52) U.S. Cl.
CPC ..... *A61M 5/172* (2013.01); *A61B 17/320758* (2013.01); *A61M 1/0031* (2013.01);
(Continued)

(58) Field of Classification Search
CPC ............ A61M 25/0105; A61M 1/0031; A61M 1/0058; A61M 5/172; A61M 2209/01;
(Continued)

(56) References Cited

U.S. PATENT DOCUMENTS 5,376,070 A * 12/1994 Purvis .................. A61M 5/172
604/31
5,573,506 A * 11/1996 Vasko .................. A61M 5/172
128/904

(Continued)

FOREIGN PATENT DOCUMENTS

CN          101094617 A      12/2007
CN          102137689 A       7/2011
(Continued)

OTHER PUBLICATIONS

Bayer Medical Care Inc., "International Search Report and Written Opinion," Int'l Patent Application No. PCT/US2014/020434, filed Mar. 4, 2014 (Jun. 5, 2014).

*Primary Examiner* — Nathan R Price
*Assistant Examiner* — Melissa A Snyder
(74) *Attorney, Agent, or Firm* — Seager, Tufte & Wickhem, LLP (57) ABSTRACT

Interventional catheter assemblies and components providing improved operational control of interventional catheters and/or operating heads of interventional catheters are provided. In general, controllers incorporate at least two operator selectable control features for controlling operation of the interventional catheter and/or an operating head, and are housed independently of the interventional catheter operating systems and other control systems, which may be provided in a housing located or locatable at a proximal region of the interventional catheter. The controller may be both dockable in and removable from the housing, and is operable in both a docked condition and a removed condition, providing flexibility and mobility in operational control during an interventional procedure.

18 Claims, 4 Drawing Sheets

(51) Int. Cl.
*A61B 17/3207* (2006.01)
*A61M 5/142* (2006.01)
*A61B 17/00* (2006.01)

(52) U.S. Cl.
CPC .......... *A61M 1/0058* (2013.01); *A61M 5/142* (2013.01); *A61B 2017/00199* (2013.01); *A61B 2017/00212* (2013.01); *A61B 2017/00221* (2013.01); *A61B 2017/00225* (2013.01); *A61B 2217/005* (2013.01); *A61B 2217/007* (2013.01); *A61M 2205/3569* (2013.01); *A61M 2209/01* (2013.01)

(58) Field of Classification Search
CPC .......... A61M 2209/086; A61M 5/1415; A61M 5/142; A61M 2205/3569; A61N 17/320758; A61B 2217/005; A61B 2217/007; A61B 2017/00212; A61B 2017/00221; A61B 2017/00199; A61B 2017/00225
See application file for complete search history.

(56) References Cited

U.S. PATENT DOCUMENTS

| | | | |
|---|---|---|---|
| 6,432,065 B1 * | 8/2002 | Burdorff | A61B 10/0275 600/566 |
| 6,565,588 B1 | 5/2003 | Clement et al. | |
| 6,676,627 B1 | 1/2004 | Bonnette et al. | |
| 6,818,001 B2 | 11/2004 | Wulfman et al. | |
| 7,018,361 B2 * | 3/2006 | Gillespie, Jr. | A61M 5/142 604/151 |
| D600,792 S | 9/2009 | Eubanks et al. | |
| 7,713,231 B2 | 5/2010 | Wulfman et al. | |
| 7,713,235 B2 | 5/2010 | Torrance et al. | |
| 7,713,240 B2 * | 5/2010 | Istoc | A61M 5/142 604/131 |
| 7,842,009 B2 | 11/2010 | Torrance et al. | |
| 7,842,990 B2 | 11/2010 | Kang | |
| 7,935,077 B2 | 5/2011 | Thor et al. | |
| 8,388,077 B2 | 3/2013 | Park | |
| 8,388,582 B2 | 3/2013 | Eubanks et al. | |
| 2003/0114869 A1 * | 6/2003 | Nash et al. | 606/159 |
| 2005/0251228 A1 | 11/2005 | Hamel | |
| 2006/0116667 A1 * | 6/2006 | Hamel | A61B 17/320068 606/1 |
| 2007/0073233 A1 | 3/2007 | Thor et al. | |
| 2010/0049119 A1 * | 2/2010 | Norman | A61M 3/0258 604/31 |
| 2010/0261979 A1 | 10/2010 | Kiani | |
| 2011/0040238 A1 | 2/2011 | Wulfman et al. | |
| 2011/0106004 A1 | 5/2011 | Eubanks et al. | |
| 2011/0112562 A1 | 5/2011 | Torrance | |
| 2012/0059270 A1 | 3/2012 | Grunwald | |
| 2012/0184955 A1 | 7/2012 | Pivotto | |

FOREIGN PATENT DOCUMENTS

| | | |
|---|---|---|
| WO | 03034898 A2 | 5/2003 |
| WO | 2006050410 A1 | 5/2006 |
| WO | 2008/042987 A2 | 4/2008 |
| WO | 2010021866 A1 | 2/2010 |
| WO | 2013134133 A1 | 9/2013 |

* cited by examiner

INTERVENTIONAL CATHETER ASSEMBLIES AND CONTROL COMPONENTS FOR INTERVENTIONAL CATHETER ASSEMBLIES

FIELD OF THE INVENTION

Interventional catheter assemblies for performing minimally invasive operations at internal body sites, such as at an internal cavity or lumen of a mammalian subject, are disclosed. The disclosure relates, more particularly, to systems and methods used for operating and controlling such interventional catheter assemblies.

BACKGROUND OF THE INVENTION

Removal of disease such as atherosclerotic plaque, thrombus and other types of obstructions and partial obstructions from internal body lumens or cavities using interventional catheters having operating heads that function to break down and/or remove occlusive material using mechanical structures such as cutter assemblies, abrasive materials and/or shaped tools, ablation instruments employing modalities such as RF, laser or radiation-induced ablation modalities, ultrasound, fluid jets or fluid agitation and the like, are well-established interventional techniques. Other types of interventional catheters may provide fluid infusion and/or aspiration alone or in combination with another diagnostic or treatment modality. Yet other types of interventional catheters may be employed for delivery of devices or compositions to an interventional site.

Many material removal devices and interventional catheters incorporate mechanical aspiration systems to remove material from the interventional site and some systems incorporate, or are used in conjunction with, other mechanisms such as distal filters for preventing removed material from circulating in the blood stream. Some interventional catheter systems incorporate or are used in conjunction with a fluid infusion system providing delivery of fluids to an interventional site. Interventional catheter systems may also incorporate or be used in conjunction with imaging systems and other types of complementary and/or auxiliary tools and features that facilitate desirable placement and operation of the system during an interventional procedure. Despite the many and varied approaches to material removal systems, many challenges remain in providing systems for removing material from an internal body site safely and reliably and without causing complications. The safety and reliability of the system, and the ability of the operator to monitor the intervention, acquire and evaluate feedback during the intervention, and control the system conveniently and with assurance and responsiveness, is critical.

Interventional catheters are generally assembled with and/or associated with or mounted to a housing providing an enclosure for drive mechanisms, fluid manifolds and management systems, and the like, with the housing generally located at a proximal region of the catheter. Some types of interventional catheters employ a single operational and control component interfacing with and mounted to the interventional catheter at a proximal region of the catheter. In devices that interface with a single operating and control component, system and operating components may be housed in the control component and user interface controls for operating the catheter may be provided on the operating and control component. Various control features for activating and operating the interventional catheter, its aspiration and/or infusion systems, and other functional systems may be provided. Status indicators, system read-outs and operating information may also be provided on interventional catheter operating and control components.

Some interventional catheter systems employ a console-type controller that houses non-disposable components such as pumps, drive systems, electrical, electronic, vacuum and fluid control systems, and the like, alone or in combination with another intermediate control device that provides operator control options and, in some cases, feedback information. In interventional catheter systems employing an intermediate control device, the intermediate control device is typically located at or near a proximal region of the interventional catheter. The intermediate control device may be positioned within or close to the sterile field during a procedure, while the console-type controller may be positioned outside the sterile field during a procedure. Interventional catheter systems employing both a console-type controller and an intermediate control device are described, for example, in PCT International Publication WO 2008/042987 A2, the disclosure of which is incorporated herein by reference in its entirety. Patients may also be monitored during an interventional procedure using separate or integrated systems, such as fluoroscopic or other visualization systems, vital sign monitoring systems, and the like.

During an interventional procedure, some of the operating and feedback systems used during the procedure are monitored audibly and/or visually following set-up and must simply be within the medical professionals' visual and/or auditory field during the intervention. Other operating and feedback systems, including at least some features of interventional catheter controller(s), are actuated and/or manipulated by an operator to position, move, operate and adjust operation of the interventional catheter during an intervention. The interventional catheter control features that require operation and manipulation during an intervention should be designed and positioned to facilitate convenient and effective operator access and control during the intervention. Providing convenient and effective access to a selection of operating and monitoring systems, or to all of the interventional catheter operating and monitoring systems, to medical personnel during an intervention is important and may be crucial to the success and efficacy of an intervention and the patient's health and recovery. The present disclosure is directed to interventional catheter assemblies and interventional catheter control systems that provide improved convenience, effectiveness and mobility during an intervention.

SUMMARY

Interventional catheter assemblies that may be employed to rapidly and effectively perform minimally invasive operations at internal body sites, such as to aspirate, irrigate, deliver devices and/or materials to, and/or to remove unwanted material from internal body sites, such as internal lumens, passageways, or cavities are disclosed. Interventional catheters assemblies disclosed herein may be adapted for delivery to and use within a variety of internal body sites, such as body cavities, body lumens or passageways such as blood vessels and vascular cavities, gastrointestinal cavities, lumens or cavities in the urinary system and in male and female reproductive organs, and other fluid cavities such as pulmonary lumens and gas exchange cavities, nasal and sinus cavities, and the like. The lumen or cavity may form a generally tubular structure, such as a blood vessel, a ureter, a fallopian tube, a nasal passageway, or another passageway.

Interventional catheter assemblies and control components described herein may be used, for example, to deliver fluids or devices to, or to remove undesired material from, native blood vessels such as native coronary, renal, cranial, peripheral and other blood vessels, as well as artificial or grafted vessels such as saphenous vein grafts, and the like. The lumen may have implanted devices such as stents in place. The lumen or cavity may be within, or in proximity to, an organ such as a kidney, gall bladder, lung or the like, or the body cavity may form part of another system, such as a lymph node, spinal canal, or the like.

Interventional catheter assemblies and control components described herein may be used, for example, for aspirating and/or irrigating target interventional sites, as well as for delivering devices or compositions to, or for removing unwanted material from, a target site in body lumens, passageways or cavities of mammalian subjects, particularly human patients. Undesired material that may be removed using interventional catheter assemblies and control components disclosed herein may be disease material such as atherosclerotic plaque, calcified plaque, thrombus, or other types of deposits, gallstones, a valve or portion thereof, undesired fluids, and the like. Interventional catheters disclosed herein may incorporate a material removal component, referred to herein as an "operating head," which is generally positioned at or near the distal region of the interventional catheter. Various types of operating heads may be used in connection with interventional catheter assemblies described, including operating heads that break down and/or remove occlusive material using mechanical structures such as cutter assemblies, abrasive materials and/or shaped tools, excision devices, ablation instruments employing modalities such as RF, laser or radiation-induced ablation modalities, ultrasound, fluid jets or fluid agitation and the like. Rotating operating heads may be operably connected to a rotatable and axially translatable drive shaft, drive system and one or more control systems. In certain embodiments, interventional catheter assemblies and control components disclosed herein are employed in the treatment of cardiovascular or peripheral artery disease (PAD) to evacuate disease material from blood vessels, including peripheral blood vessels.

Interventional catheter assemblies described herein include an elongated, flexible catheter component that is at least partially inserted into and navigated within a patient's body to an interventional site while an operator controls the system externally of the patient's body. An interventional catheter control module may house operational and/or control components such as drive motor(s), aspiration and/or infusion system(s), controllers, electronics, circuits, energy sources, and the like. A control module may also provide power to a downstream interventional catheter controller, and various control and display features may also be provided at the control module. Exemplary interventional catheter systems are described, for example, in U.S. Pat. Nos. 6,676,627, 7,713,231, 7,842,990, 7,935,077 and 8,388,582, the disclosures of which are incorporated herein by reference in their entireties.

Fluidic communication between the distal region of the catheter and externally positioned components of the interventional catheter system may be provided through one or more sealed passageways of the catheter system. Sealed aspiration and/or infusion lumens provided in an interventional catheter assembly generally interface with aspiration and/or infusion tubing, which in turn interfaces with aspiration and/or infusion systems, such as pumps, vacuum devices, infusate sources, and the like, provided in connection with operating and control systems. Other types of communication systems or pathways may also be provided for delivery of power, for rotationally driving (or otherwise operating) an operating head, for implementing various control features, and the like. An operating head may be driven or controlled using electrical systems, radio frequency and other remote control systems, mechanical systems, magnetic systems and other systems or modalities suitable for remote operation of an operating head. The operating head may also incorporate features providing additional functionalities such as ultrasound guidance, various types of imaging features, and the like. The interventional catheter system may be used in conjunction with a flexible guide wire that is navigated through internal passageways, such as blood vessels, to a target material removal site. Other methods that may be employed for guiding and steering the operating head include, but are not limited to, radio frequency systems, stereotactic systems, magnetic systems, remote control systems, and the like. The system components described herein are described as exemplary components and are not intended to limit the scope of the present disclosure.

Control components may be used with and integrated into interventional catheter systems of many different types, permitting a user to operate and control interventional catheter systems in a safer, more effective and more convenient manner. In general, control components are mounted to or contained within a control housing that communicates with the elongated catheter and is positioned or positionable at a proximal region of the catheter. In some embodiments, the catheter may be permanently mounted to the control housing at a proximal region of the catheter, such that the catheter and the control housing provide an integrated interventional catheter assembly. In some embodiments, the catheter may be mountable to and detachable from the control housing at a proximal region of the catheter. In embodiments in which the catheter and control housing are detachable from one another, the control housing may be provided as a re-usable component and, in some embodiments, it may be used with catheters having different sizes, capabilities, and the like. The operation of interventional catheter assemblies, in general, may involve activation or adjustment of one or more control features associated with one or more control housing(s) located at a proximal region of the catheter, and may additionally involve activation or adjustment of one or more control features associated with a control module separate from the control housing.

In one embodiment, a control component is dockable in and removable from one or more control housing(s) enclosing interventional catheter operating systems and is operable in both a docked condition and a removed, or undocked, condition. This arrangement allows an operator to control operation of the interventional catheter from the location of one or more control housing(s) enclosing interventional catheter operating systems, or from a location separated and/or remote from one or more control housing(s) enclosing interventional catheter operating systems, at the option of the operator. This feature facilitates operator mobility during an interventional procedure while allowing the operator to continue controlling operation of the interventional catheter, which may contribute to the safety and efficacy of the procedure. This feature also facilitates smooth exchanges of operators during an interventional procedure without requiring shifting of personnel and equipment.

The control component generally provides at least two operator selectable control features for controlling operation of an interventional catheter. The control component may be provided as a handheld device, designed and configured to be easily held, moved and operated by an ambulatory operator during an intervention. The convenient portability of the control component allows one or more operator(s) to change position during an intervention without moving the control housing or interventional catheter, and it also allows the interventional catheter to be operated by different personnel during an intervention without substantial maneuvering, while interventional catheter operating systems, mounted in one or more housings or consoles, may be set up and positioned within or outside the sterile operating field prior to an intervention and remain substantially stationary during an intervention.

Control features provided on control components disclosed herein may include passive operator interface feature(s) for operator information and monitoring purposes, and/or may include active control features that are selectable and/or adjustable by an operator to change an interventional catheter operating condition, feature, position, function, setting, or the like. Examples of control features that may be provided on control components include various types of status indicator(s), actuator(s) (e.g., operable switches), adjustment mechanism(s), readout(s), and the like. Control components, along with their various incorporated control features and functions, are designed to be fully integrated with interventional catheter systems, providing improved operator convenience during interventional procedures, better accessibility of control features, greater flexibility in operator positioning during interventions, and improved visibility and selectability of interventional catheter system functions and parameters. The disclosed control systems therefore provide safer and more convenient operation and control of interventional catheter systems.

In some embodiments, control components of the present disclosure may serve as the primary user interface for an operator during operation of an interventional catheter system. In other embodiments, control components may provide auxiliary control features and may be used in combination with one or more additional controllers during operation of an interventional catheter system. Control components may be operably connected to or interface with another interventional catheter control system, such as a control console provided as a reusable system component housing a power supply, aspiration and/or infusion sources or systems, control circuitry, software, user interfaces, and various operational status indicators, displays, alarms, and the like. In interventional catheter systems utilizing a control console, certain operating features and parameters may be preset or programmable via the console, and the console may provide feedback and monitoring displays providing status information relating to system operation and operating parameters, while the control component provides access to operating and control features that are activated, set and/or adjusted by the operator during an interventional procedure.

Some interventional catheter systems incorporate a primary or intermediate controller mounted at a proximal end of the interventional catheter that houses catheter operating systems and may provide an operator interface for monitoring and control features. Control components may provide a primary or auxiliary user interface for monitoring and controlling interventional catheter operations in these types of interventional catheter systems as well. Control components may be operably connected to or interface with a controller mounted at a proximal end of the interventional catheter, with the control component providing access to operating and control features that are activated, set and/or adjusted by the operator during an interventional procedure.

Interventional catheter operating systems, such as mechanical components, operating head operating components, motor drive components, electrical components, electromagnetic components, aspiration components, infusion components, timing mechanisms and the like, are generally mounted in one or more housing assemblies, with an integrated user interface or one or more separate control components providing an operator interface for displaying monitoring feature(s) such as status indicator(s) and for selectably operating actuator(s) (e.g., operable switches), adjustment mechanism(s), readout(s), or the like.

Control components as disclosed herein are movable during an interventional procedure with respect to both the interventional catheter itself, and with respect to operating systems located in a control housing assembly. In one embodiment, operable communication between a control component and a control housing assembly is provided by a wired connection, thereby providing a control component that is tethered to an interventional catheter and/or interventional catheter control housing by means of a cable. In other embodiments, operable communication between a control component and a control housing assembly is provided by a wireless connection, providing a control component that is untethered to and operable at various distances from an interventional catheter and an associated control housing. In this embodiment, the operator is provided with considerably more flexibility in positioning of the control component relative to the position of the interventional catheter and its operating systems and improved freedom of movement within the operating room. Ambulatory, handheld control components are also easily and conveniently used by different medical professionals during an intervention without requiring repositioning of the professionals during the intervention. Any type of wireless communication technology well known to those skilled in the art may be used to establish and maintain the wireless connection and provide operable communication between an untethered control component and the operating systems.

Within the broad scope of the present disclosure, a wide variety of control component types and features that are useful in connection with various types of interventional catheters and that are known to those skilled in the art may be incorporated in control components described herein, allowing a user to view, assess, evaluate, manage, select, adjust, or otherwise monitor, operate and control important parameters affecting interventional catheter system operation and performance. Examples of control components that may be provided on controllers include but are not limited to various kinds of visual and/or audible status indicators, e.g. light emitting diodes (LEDs), gauges, meters, alarms, and the like, various kinds of operable switches, e.g. push buttons, toggles, touch pads, and the like, as well as various types of adjustment mechanisms, e.g. dials, sliders, and the like, and combinations of the foregoing. Similarly, any number of other control features may be optionally incorporated into the control components described herein, being configured to provide a wide variety of monitoring and control functions (e.g. indicators, switches, adjustable mechanisms, etc.). These optional control features may be distributed between and arranged in a variety of configurations to further increase usability, safety, convenience and/or functionality of control systems.

For convenience and ease of use, it may be desirable to configure a control component providing substantially all of the monitoring and control features necessary to operate and control the interventional catheter assembly during an interventional procedure. In other embodiments, it may be desirable to have a control component in operable communication with, and generally positioned intermediate, an interventional catheter operating head and a control console, and a second controller in operable communication with the control component. In this embodiment, certain activation and/or control features may be provided on both an ambulatory control component and on a system control console or housing, allowing the user to monitor and/or adjust certain operating and control condition(s), feature(s), position(s), function(s), setting(s), and the like from either the control component or a stationary console or controller. Accordingly, based on various considerations such as the type of interventional catheter system, the clinical procedure, the patient's condition, safety factors, ergonomics, medical staffing during an intervention, or the like, multiple and duplicative control features may be designed and configured in integrated control system described herein.

BRIEF DESCRIPTION OF THE DRAWINGS

Illustrative embodiments of various aspects and elements of the present disclosure are described in greater detail in the following detailed description with reference to the accompanying illustrations and images, which are not intended to limit the scope of the disclosure in any way.

DETAILED DESCRIPTION

Figure 1:
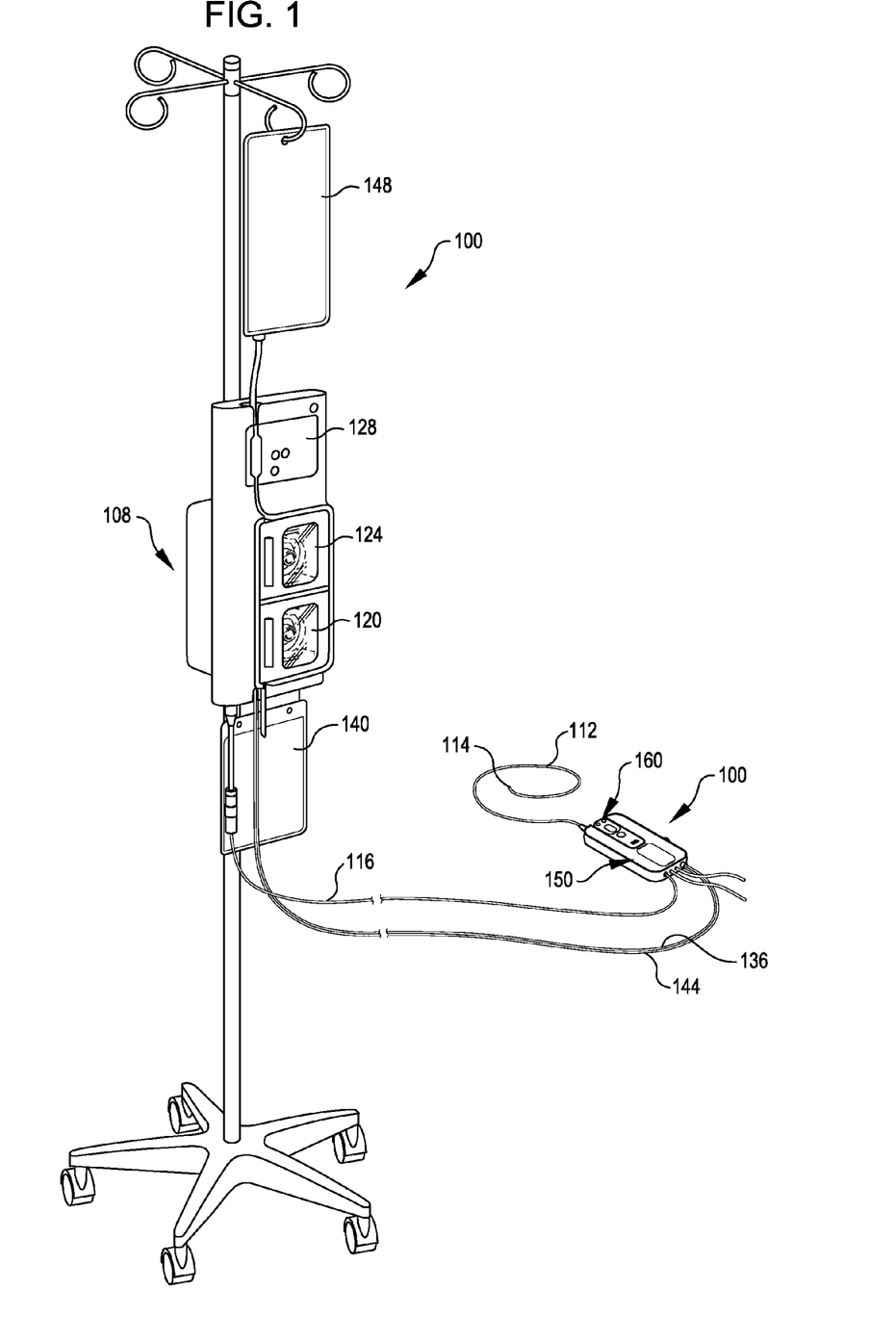
FIG. 1 shows an exemplary interventional catheter assembly comprising an interventional catheter associated with a housing enclosing one or more interventional catheter operating systems, a control component providing operator selectable control features docked in the housing according to one embodiment.

FIG. 1 shows an exemplary interventional catheter assembly 100 in which a control housing assembly 150 and dockable control component 160 are provided. Illustrative interventional catheter assembly 100 comprises interventional catheter 112 having an (optional) operating head 114 in proximity to its distal end. Control housing assembly 150 incorporates various interventional catheter operating systems and components, such as fluid management systems, and is associated with control component 160, shown docked in housing assembly 150. In the embodiment illustrated in FIG. 1, interventional catheter assembly 100 interfaces with a control console 108 incorporating other system operating components, aspiration and infusion pump systems, and supporting conduits and reservoirs for aspiration and infusion fluids. Electrical cable 116 provides electrical power from the control console 108 to intermediate control housing assembly 150 and aspiration and infusion conduits 136, 144, respectively, provide fluidic communication between control housing assembly 150 and the aspiration and infusion systems 120, 124, respectively, provided in control console 108.

In the embodiment illustrated in FIG. 1, control console 108 is a reusable system component that contains an aspiration system 120 such as a peristaltic aspiration pump for aspiration of fluid and debris and an infusion system 124 such as a peristaltic infusion pump for infusion of one or more fluids at desired flow rates. Control console 108 also incorporates a control panel 128 providing a user interface for operating and/or monitoring systems housed in control console 108 and various system operating conditions. In the embodiment shown in FIG. 1, aspiration conduit 136 provides a sealed lumen connecting an aspiration lumen or channel of interventional catheter assembly 112 to the aspiration system 120 and an aspiration collection receptacle 140. The aspiration path traverses the interventional catheter 112, control housing assembly 150 and aspiration system or source 120. Similarly, infusion conduit 144 provides a sealed lumen connecting an infusion port positioned at or near the distal end of the interventional catheter 112 and an infusion lumen or channel of interventional catheter 112 to the infusion system 124 and infusate reservoir 148. In this embodiment, the aspiration and infusion conduits are provided as integral features of interventional catheter assembly 100. As used herein, "proximal" refers to a direction toward the system controls and the operator along the path of the catheter system, and "distal" refers to the direction away from the system controls and the operator along the path of the catheter system toward or beyond a terminal end of the catheter and/or an operating head.

While a separate control console 108 and housing assembly 150 are illustrated for exemplary purposes in FIG. 1, it will be appreciated that all or substantially all of the interventional catheter system operating requirements and controls may be provided in a single housing, and that either control console 108 or control housing assembly 150 may incorporate substantially all of the system operating and control requirements and communicate with one or more infusion sources and aspiration receptacles, as appropriate.

Simple interventional catheter systems may provide aspiration and/or infusion functions, providing fluids to a desired interventional site using an infusion system and/or removing fluid and debris from an interventional site using an aspiration system. More complex interventional catheter systems may incorporate an operating head positioned or positionable in proximity to a distal end of the interventional catheter and communicating with a material removal or ablation operating system located in housing assembly 150 and/or in a separate console, such as control console 108. Interventional catheter 112, as illustrated in FIGS. 1-4, is sized and configured for insertion into a patient and guidance to an internal interventional site and typically comprises an elongated, flexible catheter. Interventional catheter 112 may also incorporate aspiration and/or infusion lumens or channels providing fluidic communication between a distal end of the interventional catheter positioned at a site of intervention and proximally positioned aspiration and/or infusion components of the interventional catheter or its associated control and housing assemblies.

In the embodiment illustrated in FIG. 1, control housing assembly 150 is operably connected to control console 108 via electrical cable 116, through which power and electronic communications are transmitted, and is also operably connected to the proximal end of interventional catheter assembly 112. Aspiration conduit 136 provides a sealed lumen communicating between an aspiration collection receptacle 140 (positioned at its proximal end) and an aspiration lumen in interventional catheter assembly 112, providing an aspiration conduit for fluids and debris from one or more aspiration ports provided at or near the interventional catheter operating head and the collection receptacle. Similarly, infusion conduit 144 provides a sealed lumen communicating between an infusate reservoir 148 and an infusion lumen in interventional catheter assembly 112, providing an infusion conduit to deliver infusate to a desired interventional site near the distal end of the interventional catheter assembly and/or operating head. In the embodiments illustrated in FIGS. 1-4, control component 160 provides operator interfaces for activating, monitoring and/or controlling interventional catheter features and functions during an interventional procedure. It will be appreciated that some interfaces for activation, monitoring and/or controlling interventional catheter features and functions may additionally or alternatively be provided in association with interventional catheter housing assembly 150 and/or control console 108.

Figure 2:
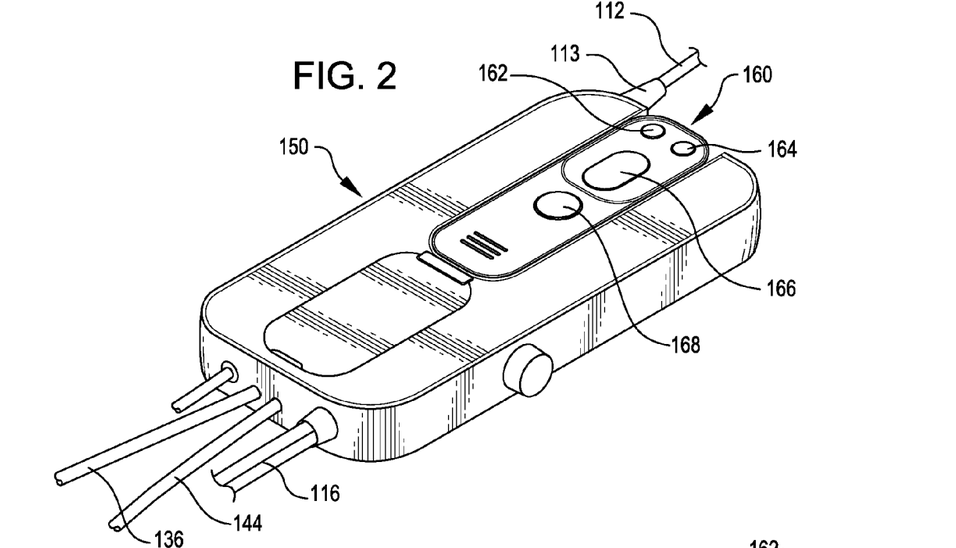
FIG. 2 is a schematic perspective view illustrating an enlarged view of the housing enclosing one or more interventional catheter operating systems and control component providing operator selectable control features docked in the housing according to one embodiment.
Figure 3:
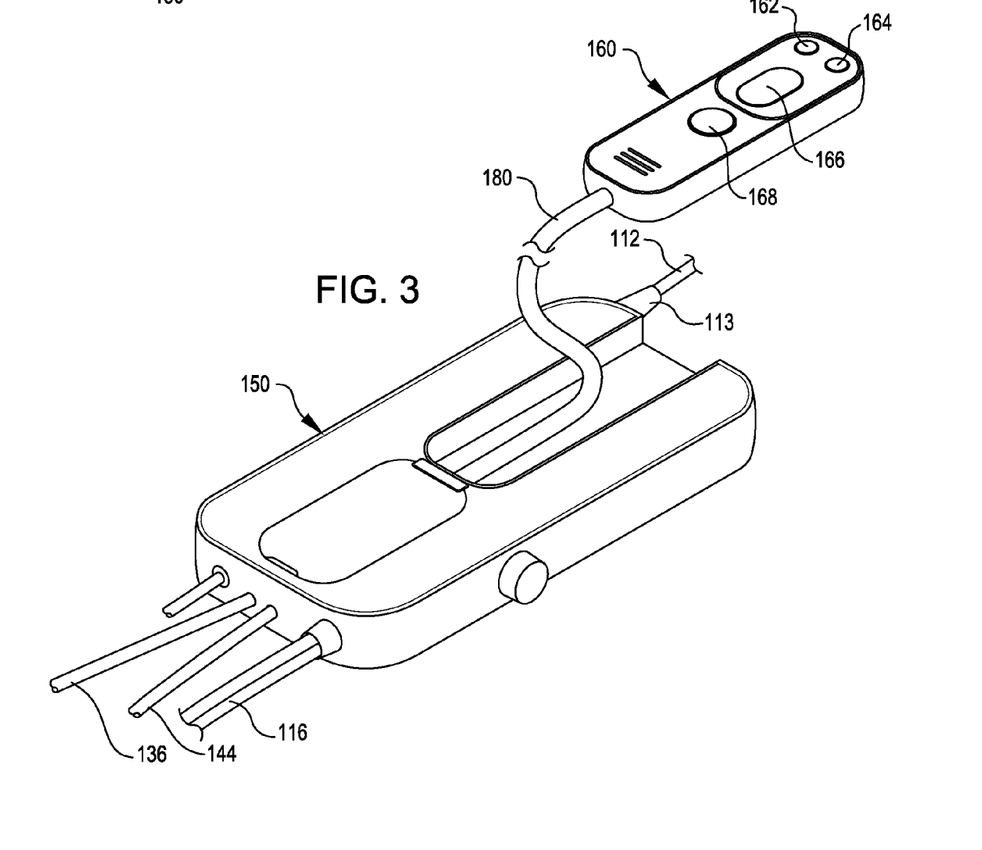
FIG. 3 is a schematic perspective view showing a housing and control component similar to that shown in FIG. 2, with the control component undocked and separate from the housing.

FIGS. 2 and 3 show enlarged schematic perspective views of control housing assembly 150 and control component 160 according to one embodiment of the present disclosure. Control housing assembly 150 is operably connected to a proximal end of interventional catheter 112 at feedthrough 113 and, in embodiments incorporating a control module, is also connected to control console 108 via electrical cable 116, aspiration conduit 136 and/or infusion conduit 144. In alternative embodiments, control housing assembly 150 may serve as a stand-alone operating and control device and may have appropriate cable(s) and conduit(s) for connection to electrical power, aspiration and infusion sources, and the like. Control component 160 is shown in a docked condition with respect to control housing assembly 150 in FIG. 2 and is shown in an undocked, removed condition in FIGS. 3 and 4, while remaining operably connected to operating systems housed in control housing assembly 150 via wired connection 180 (FIG. 3) or wirelessly, as illustrated schematically in FIG. 4. In alternative embodiments, control component 160 may be operably connected to or communicate with control console 108 or another interventional catheter control or housing component.

Control housing assembly 150 provides an interior space enclosing various system components and, in some embodiments, is permanently mounted at a proximal end of the interventional catheter 112 at feedthrough 113. In alternative embodiments, interventional catheters may be mountable to and removable from housing assembly 150, and housing assembly 150 may be provided as a re-usable system component. In general, housing assembly 150 has a substantially rigid external structure enclosing an interior space containing various operational systems, such as one or more drive motor(s) used for driving (e.g., translating and/or rotating) the interventional catheter and/or operating head, other drive mechanisms for operating other types of operating heads, associated electro-mechanical components, mechanical and fluid control components and manifolds associated with aspiration and/or infusion systems and conduits, as well as other types of electro-mechanical components, circuit boards, data processors, communication ports, and the like, necessary or desirable for the operation of interventional catheter 112 and operating head 114, and for communication and integration with other components of interventional catheter assembly 100. In some embodiments, all or substantially all of the operating systems necessary for operation of interventional catheter 112 are provided in housing assembly 150.

A proximal end of interventional catheter 112 is connected to housing assembly 150 at feedthrough 113. Feedthrough 113 is typically a flexible, rotating and/or articulating joint that is designed to allow the interventional catheter and its constituent components, such as an internal rotatable drive shaft for driving the operating head as well as aspiration and/or infusion lumens, to pass into the housing assembly and operably connect with a drive motor and fluid control components located inside the housing assembly. Housing assembly 150 is typically positioned within the sterile field during an intervention, and interventional catheter 112 is typically long enough that a length of the catheter that remains outside the body following positioning of the operating head at a desired interventional site allows flexibility in positioning housing assembly 150.

Control component 160, as shown in the exemplary embodiments of FIGS. 2 and 3, may be provided as a stand-alone or auxiliary controller for operating and monitoring the operation of interventional catheter 112 and operating head 114. Control component 160 is preferably designed, configured and sized as a handheld device that can be easily held by an operator and manipulated during operation of the interventional catheter using one hand. In the embodiments shown in FIGS. 2 and 3, control component 160 is provided as a separate component operably connected to and both dockable in and removable from housing assembly 150. Control component 160 is preferably operable in both a docked and undocked condition.

FIG. 2 shows control component 160 in a docked condition, mounted in a recess provided in control housing assembly 150, providing operator control of selectable operations and features from the location of the housing assembly. In the embodiment illustrated in FIG. 2, control component 160 is dockable within a mating recess of control housing assembly 150 and, when docked, is stably mounted within the recess and provides a substantially smooth and continuous outer surface of housing assembly 150. In alternative embodiments, control component 160 or housing assembly 150 may alternatively or additionally incorporate one or more channel(s), track(s), clip(s), snap(s) or clamp(s), or other mechanical attachment feature(s), that allow control component 160 to be detachably mounted on or associated with housing assembly 150 in a stable manner, or to be detachably and stably mounted to another mounting location within or outside the sterile operating field during an interventional procedure.

FIG. 3 illustrates control component 160 in an undocked condition, moved away and operable a distance from control housing assembly 150 via electrical cable 180. The length of cable 180 may be fixed or variable, and is sufficient to ensure there is adequate cable length to accommodate the anticipated usable range of working distances that control component 160 may be placed from housing assembly 150. Cable 180 is preferably at least about 10 cm long and may be from about 20 cm to about 200 cm long, or more. In some embodiments, it may be desirable that cable 180 is configured having extension and/or retraction features such as a spring actuated spool or other automatic extension and retraction feature known to those skilled in the art for conveniently managing its usable length.

In the embodiment illustrated in FIGS. 2 and 3, control component 160 has four user actuatable control features 162, 164, 166 and 168 provided on a control surface and configured to be conveniently accessible to an operator. In this case, controllers 162, 164 are push button activation and/or selection switches providing user selection of different modes of operation. In one embodiment, selection button 162 may be pushed by an operator to select one mode of operation of the interventional catheter, such as operation of an operating head in a first mode (e.g., a smaller diameter cutter mode), while selection button 164 may provide selection of a different operating head mode (e.g., a larger diameter cutter mode). In alternative embodiments, selection buttons may be provided for selection of rotational direction of a rotational drive system, rotational speed, or the like. Indicators may be provided in association with the selection buttons to clearly indicate the operating mode selected. Indicators such as colored indicators, lights, or the like, may be activated when a selection button is activated.

In some embodiments, selection buttons 162, 164 may provide both selection and activation of an operating mode. In other embodiments, selection buttons 162, 164 may provide operator selection of an operating mode, while activation button 166 provides operator activation of the interventional catheter. Various operating modes may be available in different types of interventional catheter assemblies, and it will be appreciated that additional selection buttons may be provided, and that operating mode selection may control a variety of different operating mode parameters. In one embodiment, for example, operation of the interventional catheter in the mode selected by one of buttons 162, 164 commences upon operator actuation of activation button 166 and continues for as long as the operator depresses activation button 166. In the embodiment illustrated in FIGS. 2-4, activation button 166 controls operation of the interventional catheter in an interventional operating mode. In this embodiment, selector 168 may operate a retraction mode may be provided, for example, for rotating the operating head at a different rate of rotation or in a different direction of rotation during withdrawal of the operating head and the interventional catheter following completion of an intervention.

Figure 4:
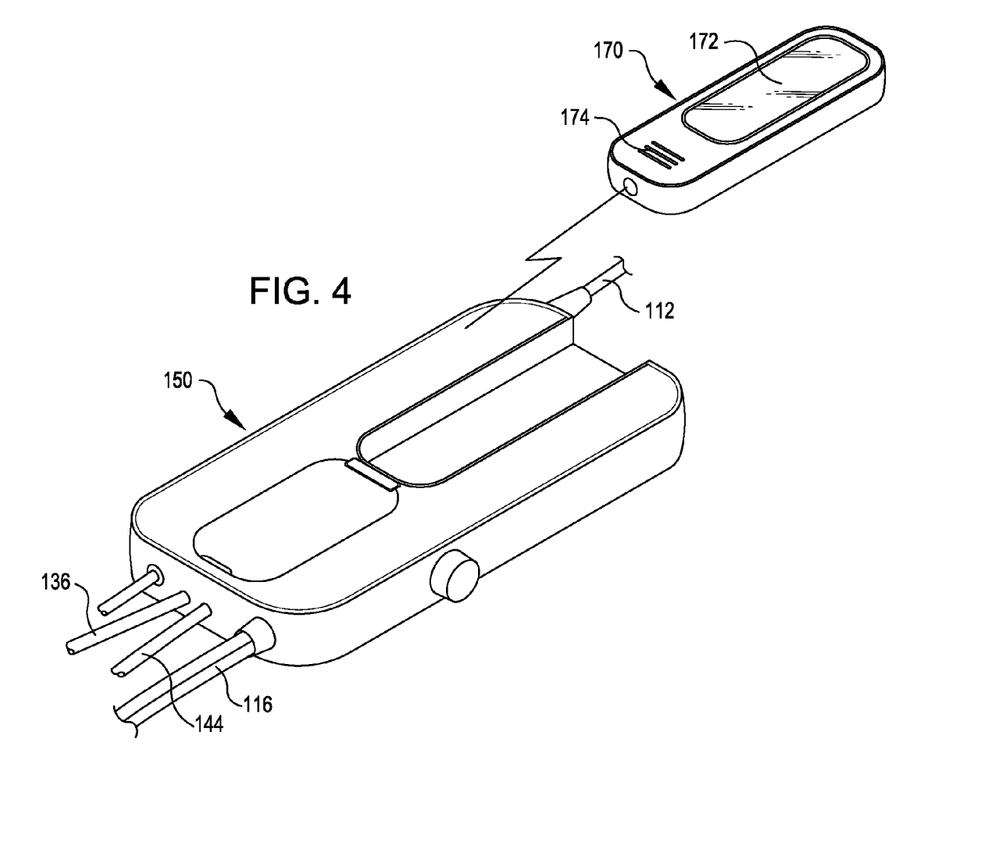
FIG. 4 is a schematic perspective view showing a housing and control component having similarities to that shown in FIG. 2, with a wirelessly operated control component undocked and separate from the housing.

FIG. 4 shows a schematic perspective view of a control component 170 according to another embodiment of the present disclosure in which the previously illustrated cable has been replaced by wireless connectivity, illustrated schematically, providing operable communication between control component 170 and operating systems provided in a housing assembly 150, a control module, or another operational component. The wireless communications technology necessary to implement wireless connectivity and its associated operational functionality are designed, constructed and incorporated into both control component 170 and components with which it communicates. Wireless connectivity technology is well known to those skilled on the art of remotely controlled electronics, involving one or more transmitters, receivers, amplifiers, signal processors, control circuitry, battery power sources, and the like.

In one embodiment, control component 170 illustrated in FIG. 4 may comprise a display 172 that provides information relating to interventional catheter operation and/or interventional site conditions, patient vital sign information, or the like to an operator on an intermittent or real-time basis. In some embodiments, display 172 may be provided as a touch screen display or another type of display device providing operating information and/or conditions to an operator, as well as interventional catheter operating capability. Touch screen controls for operating various aspects of an interventional catheter, and for actuating and controlling various interventional catheter operating parameters, may thus be provided on control component 170. In some embodiments, a control component may provide both an operable display, including a touch screen display, and actuatable buttons, as described previously. Audio output and/or input devices 174 may also be provided on or associated with control component as disclosed herein.

Figure 5:
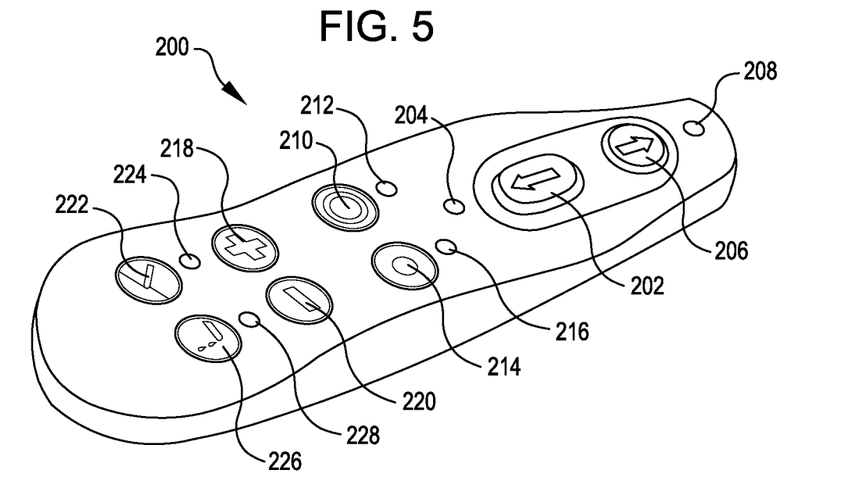
FIG. 5 is a schematic perspective view showing another embodiment of a control component of the present disclosure.

FIG. 5 shows a schematic perspective view of another embodiment of a control component 200 of the present disclosure, isolated from the housing assembly. It will be appreciated that control component 200 may be dockable in and removable from a housing assembly, using either a wired or wireless configuration, and operable in both a docked and a removed condition, as previously described. In the embodiment illustrated in FIG. 5, control component 200 provides more comprehensive control functionality for controlling all or substantially all of the operations of an interventional catheter during an intervention.

In the embodiment illustrated in FIG. 5, control component 200 includes an interventional catheter activation switch 202, as well as a retraction mode switch 206. Indicators 204 and 208 may be provided and located in proximity to activation switch 202 and retraction switch 208, respectively, to provide a visual indication of the operating status of the interventional catheter and/or operating head. Control component 200 also incorporates operating mode switches 210, 214 and associated indicators 212, 216, respectively. Operating mode switches 210, 214 may control an operating head size, operating mode or condition, or other user selectable control features. Operating switches 218, 220 may be provided for increasing and/or decreasing an operating parameter, such as increasing and/or decreasing a rotational rate of the catheter and/or operating head. Control component 200 additionally incorporates activation switches for operating aspiration and infusion systems, namely aspiration activation switch 222 and infusion activation switch 226. Each of these switches may be located in proximity to visual indicators, such as aspiration indicator 224 and infusion indicator 228.

Control component 200 is illustrative of a control component that supports and provides comprehensive control of all or substantially all of the control features required to operate a rotational, aspirating and infusing interventional catheter. It will be appreciated that other controls, switches, indicators, readouts, and the like may be provided on or in association with control component 200. In systems that accommodate multiple infusion sources, for example, an appropriate user selectable infusion source switch may be provided. Additional controls may be provided to adjust the rate and/or volume, or other features, of the aspiration and infusion systems of the interventional catheter system. In some embodiments, the control component may additionally incorporate monitoring features, such as monitors providing real-time readouts of rotational rates, aspiration and/or infusion pressure, rate, and/or cumulative volumes, vital sign monitoring information, and the like.

Figure 6:
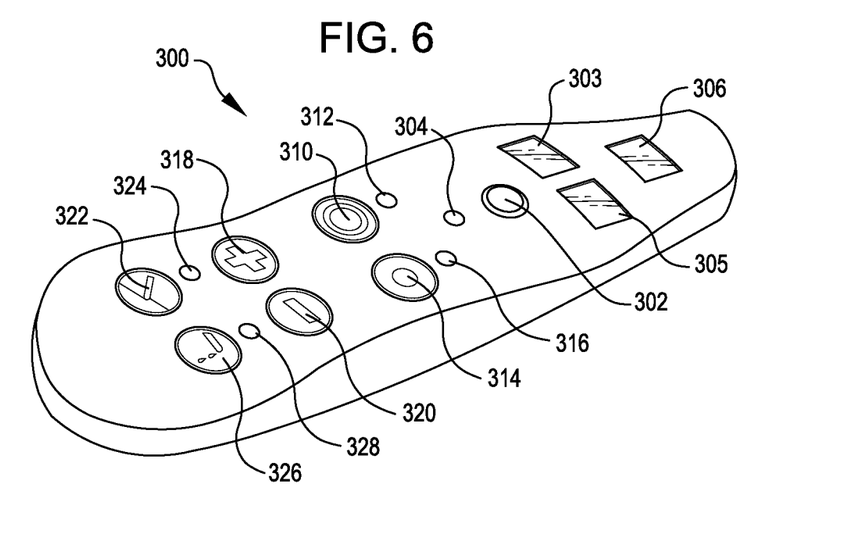
FIG. 6 is a schematic perspective view showing yet another embodiment of a control component of the present disclosure.

FIG. 6 illustrates a schematic perspective view of another embodiment of an exemplary control component 300 of the present disclosure, isolated from the housing assembly. It will be appreciated that control component 300 may be dockable in and removable from a housing assembly, using either a wired or wireless configuration, and operable in both a docked and a removed condition, as previously described. In the embodiment illustrated in FIG. 6, control component 300 provides more comprehensive control functionality for controlling all or substantially all of the operations of an aspirating and/or infusing interventional catheter during an intervention.

In the embodiment illustrated in FIG. 6, control component 300 includes an interventional catheter activation switch 302 and an indicator 304 located in proximity to activation switch 302 to provide a visual indication of the operating status of the interventional catheter and/or operating head. Control component 300 also incorporates operating mode switches 310, 314 and associated indicators 312, 316, respectively. Operating mode switches 310, 314 may control an operating mode or condition, or other user selectable control features. Control component 300 additionally incorporates activation switches for operating aspiration and infusion systems, namely aspiration activation switch 322 and infusion activation switch 326. Each of these switches may be located in proximity to visual indicators, such as aspiration indicator 324 and infusion indicator 328. Operating switches 318, 320 may be provided for increasing and/or decreasing an operating parameter, such as increasing and/or decreasing an aspiration and/or infusion flow rate or volume. Additional operating switches may also be provided.

Control component 300 additionally provides operating status indicators or readouts 303, 305, 306 that report current operating parameters, conditions, or the like to the user. In one embodiment, readouts may be provided for reporting, on a substantially continuous basis, aspiration and/or infusion rates, volumes, pressures, or the like. The operator may thus monitor aspiration and/or infusion parameters and adjust aspiration and/or infusion pressure, flow rates, flow volumes, pressures, or the like, as a procedure progresses, from control component 300. In other embodiments, readouts 303, 305, 306 on control component 300 may report parameters or conditions to the operator such as elapsed device operating time, temperature at the site of intervention, infusate supply level, and the like.

Control components such as exemplary components 160, 170, 200 and 300 may communicate and interface with additional control components, operating systems, and the like provided elsewhere in association with an interventional catheter assembly, and with other systems such as vital sign monitoring systems, used during interventional catheter procedures. Operating features that are selectable using the control component may also be selectable, for example, from an intermediate control component such as control housing assembly 150, or from a control module.

User selectable control features are generally provided in a configuration such that they are easily distinguishable from the control component housing, and from one another, both visually and by tactile sensation. Thus, multiple user selectable control features may have different sizes, shapes, colors textures, markings, or the like. The size and positioning of control component 160 or 170 or 200 or 300 relative to housing assembly 150, and interventional catheter 112, as well as any control console(s), and the availability and arrangement of the control features configured as part of control component 160, 170, 200 and 300 are important design features that may be optimized to achieve improved user convenience, accessibility, patient safety, treatment efficiency, and so on. The configuration and profile of control components 160, 170, 200 and 300 may vary considerably depending on the type of interventional catheter and the number and type selectable operating features provided and are generally selected on the basis of various design considerations, including factors such as ergonomics, safety, ease-of-use, manufacturability, cost, and the like.

In a typical interventional procedure employing an interventional catheter as described herein, the distal portion of interventional catheter assembly 112 is inserted into the patient and navigated, e.g., through the vasculature, until the distal end of the interventional catheter (e.g., the operating head), is located in an area of an obstruction or occlusion or in proximity to material desired to be removed. One or more operators carries out the desired treatment by manipulating interventional catheter assembly 112 (and operating head) to advance and retract the distal end of the operating catheter (e.g. operating head) relative to the desired interventional site while operating and adjusting various interventional catheter system features, functions and operational components using control component(s) 160, 170, 200 and 300.

While the present disclosure has been described with reference to the accompanying drawings in which particular embodiments are shown and explained, it is to be understood that persons skilled in the art may modify the embodiments described herein without departing from the spirit and broad scope of the invention. Accordingly, the descriptions are considered as being illustrative and exemplary of specific structures, aspects and features within the broad scope of the present disclosure and not as limiting the scope.

We claim:

1. An interventional catheter assembly comprising:
   an elongated flexible catheter sized and configured to be navigated to an internal site;
   a control console;
   a housing containing a recessed portion and one or more interventional catheter operating systems and connected to a proximal region of the elongated flexible catheter, the housing spaced away from the control console; and
   a control component shaped to fit within and mate with the recessed portion, wherein the control component communicates with one or more of the interventional catheter operating systems contained in the housing and has at least two operator selectable control features, wherein the control component is dockable in and detachable from the recessed portion and is operable to control operation of the elongated flexible catheter in both a docked condition at the housing and a detached condition away from the housing.

2. The interventional catheter assembly of claim 1, wherein the control component communicates with the one or more interventional catheter system operating systems contained in the housing by means of a wired connection.

3. The interventional catheter assembly of claim 1, wherein the control component communicates with the one or more interventional catheter operating systems contained in the housing by means of a wireless connection.

4. The interventional catheter assembly of claim 1, wherein the control component is a handheld device that provides a user interface for at least two operator selectable control features.

5. The interventional catheter assembly of claim 1, additionally comprising a rotatable drive shaft extending through the elongated flexible catheter and an operating head operably connected to a distal region of the rotatable drive shaft and located at or distal to a distal region of the elongated flexible catheter.

6. The interventional catheter assembly of claim 5, wherein the control component provides a user interface for controlling a direction of rotation of the rotatable drive shaft.

7. The interventional catheter assembly of claim 5, wherein the control component provides a user interface for controlling a rate of rotation of the rotatable drive shaft.

8. The interventional catheter assembly of claim 1, wherein the elongated flexible catheter comprises an aspiration lumen, and wherein the control component provides a user interface for activating and inactivating an aspiration system.

9. The interventional catheter assembly of claim 1, wherein the elongated flexible catheter comprises an aspiration lumen, and wherein the control component provides a user interface for adjusting or selecting a flow rate through the aspiration lumen.

10. The interventional catheter assembly of claim 1, wherein the elongated flexible catheter comprises an infusion lumen, and wherein the control component provides a user interface for activating and inactivating an infusion system.

11. The interventional catheter assembly of claim 1, wherein the elongated flexible catheter comprises an infusion lumen, and wherein the control component provides a user interface for adjusting or selecting a flow rate through the infusion lumen.

12. The interventional catheter assembly of claim 1, wherein the elongated flexible catheter comprises an infusion lumen, and wherein the control component provides a user interface for controlling a volume of infusion.

13. The interventional catheter assembly of claim 1, wherein the elongated flexible catheter comprises an infusion lumen, and wherein the control component provides a user interface for selecting an infusate from a plurality of infusion sources.

14. The interventional catheter assembly of claim 1, wherein the control component provides a visual indication of at least one operating parameter.

15. The interventional catheter assembly of claim 1, wherein the control component displays vital sign monitoring information.

16. The interventional catheter assembly of claim 1, wherein the elongated flexible catheter can aspirate, irrigate, deliver devices to, deliver materials to, and/or remove unwanted material from, internal body sites during an intervention.

17. An interventional catheter housing assembly comprising: a control console including at least one pump; at least one housing spaced away from the control console, wherein the housing includes a recessed portion and containing one or more interventional catheter operating systems and a control component shaped to fit within and mate with the recessed portion, wherein the control component communicates with the one or more interventional catheter operating systems contained in the housing and includes at least two operator selectable control features, wherein the control component is dockable in and detachable from the recessed portion and is operable in both a docked condition at the housing and a detached condition away from the housing.

18. An interventional catheter assembly, comprising:
an interventional catheter, the catheter including a proximal portion and a distal portion;
a control housing assembly connected to the proximal portion of the interventional catheter, the control housing assembly including a recessed portion;
a control component configured to mate with and be detachable from the recessed portion of the control housing; and
a control console including at least one pump;
wherein the control housing assembly is spaced away from the control console;
wherein the control console and the control housing assembly are connected via at least one tubular member.

* * * * *